United States Patent
Günther et al.

(10) Patent No.: US 9,827,358 B2
(45) Date of Patent: Nov. 28, 2017

(54) SEALING MEANS FOR SEALING A VOLUME OF A MEDICAL TREATMENT ARRANGEMENT AGAINST ANOTHER VOLUME, AS WELL AS AN ARRANGEMENT AND A METHOD

(75) Inventors: Goetz Günther, Oberursel (DE); Markus Koehler, Oberursel (DE); Uwe Lapp, Butzbach (DE); Martin Lauer, St. Wendel (DE); Ralf Mueller, Bad Homburg (DE); Peter Scheunert, Friedrichsdorf (DE); Wolfgang Schulz, St. Wendel (DE); Udo Waeber, Offenbach (DE); Manfred Weis, St. Wendel (DE); Andrea Günther, legal representative, Oberursel (DE); Richard Robert Bernd Günther, legal representative, Stuttgart (DE); Gesa Dagmar Günther, legal representative, Stuttgart (DE)

(73) Assignee: Fresenius Medical Care Deutschland GmbH, Bad Homburg (DE)

(*) Notice: Subject to any disclaimer, the term of this patent is extended or adjusted under 35 U.S.C. 154(b) by 187 days.

(21) Appl. No.: 13/255,658

(22) PCT Filed: Mar. 10, 2010

(86) PCT No.: PCT/EP2010/001455
§ 371 (c)(1),
(2), (4) Date: Nov. 21, 2011

(87) PCT Pub. No.: WO2010/102784
PCT Pub. Date: Sep. 16, 2010

(65) Prior Publication Data
US 2012/0080437 A1    Apr. 5, 2012

(30) Foreign Application Priority Data
Mar. 10, 2009 (DE) .................. 10 2009 012 632 U

(51) Int. Cl.
*A61M 1/14* (2006.01)

(52) U.S. Cl.
CPC .......... *A61M 1/14* (2013.01); *A61M 2205/11* (2013.01); *A61M 2205/122* (2013.01)

(58) Field of Classification Search
CPC ........ A61M 2205/122; A61M 2205/12; A61M 2205/11; A61M 1/14
(Continued)

(56) References Cited

U.S. PATENT DOCUMENTS

| 4,319,614 A | * | 3/1982 | Boice ........................... 141/381 |
| 4,383,484 A | * | 5/1983 | Morrey ..................... 102/275.3 |

(Continued)

FOREIGN PATENT DOCUMENTS

| CN | 1127478 A | 7/1996 |
| CN | 1321103 A | 11/2001 |

(Continued)

OTHER PUBLICATIONS

PCT International Search Report from PCT/EP2010/001455 dated Jul. 12, 2010.
(Continued)

*Primary Examiner* — Stephen Castellano
(74) *Attorney, Agent, or Firm* — Fish & Richardson P.C.

(57) ABSTRACT

Disclosed is a sealing device for sealing at least one first volume of an arrangement for the treatment of at least one medical fluid against at least one second volume, wherein the first volume is provided for receiving at least one external functional device. The sealing device includes at least one first connection device whereby the sealing device may be connected to the arrangement. In addition an arrangement and a method are disclosed.

23 Claims, 7 Drawing Sheets

(58) Field of Classification Search
USPC ........ 220/780; 210/321.7, 321.8, 321.9, 188, 210/195.2, 321.6; 604/6.09, 4.01, 5.01, 604/6.07, 6.1, 6.11
See application file for complete search history.

(56) References Cited

U.S. PATENT DOCUMENTS

| | | | |
|---|---|---|---|
| 4,388,998 A * | 6/1983 | Underwood et al. | 220/780 |
| 4,838,303 A * | 6/1989 | Goans | 137/423 |
| 6,612,456 B1 * | 9/2003 | Hundley et al. | 220/254.3 |
| 2003/0220598 A1 | 11/2003 | Busby et al. | |
| 2005/0126998 A1 | 6/2005 | Childers | |
| 2005/0167430 A1 * | 8/2005 | Varadarajan | 220/258.1 |
| 2005/0209563 A1 | 9/2005 | Hopping et al. | |
| 2005/0230292 A1 | 10/2005 | Beden et al. | |
| 2007/0112297 A1 | 5/2007 | Plahey | |
| 2010/0200486 A1 | 8/2010 | Günther et al. | |
| 2012/0080437 A1 | 4/2012 | Guenther et al. | |

FOREIGN PATENT DOCUMENTS

| | | |
|---|---|---|
| DE | 100 34 711 A1 | 2/2002 |
| DE | 101 57 924 C1 | 6/2003 |
| DE | 102 24 750 A1 | 12/2003 |
| DE | 10 2007 042 964 A1 | 3/2009 |
| DE | 10 2009 012 633 A1 | 9/2010 |
| EP | 1314443 | 5/2003 |
| JP | H07116245 A | 5/1995 |
| JP | 08-507121 A | 7/1996 |
| JP | 2006097314 | 4/2006 |
| JP | 2005528168 | 9/2008 |
| JP | 2010538687 | 12/2010 |
| WO | 0117650 | 3/2001 |
| WO | WO 01/17650 A1 | 3/2001 |
| WO | WO 2005/042065 A2 | 5/2005 |
| WO | WO 2009/006501 A2 | 1/2009 |
| WO | 2010 066441 | 6/2010 |
| WO | 2010/102790 A2 | 9/2010 |

OTHER PUBLICATIONS

Compact Oxford Dictionary and Thesaurus, Third Edition, Oxford University Press, 2009, pp. 389, 833-834.

Japanese Search Report by Registered Searching Organization in Japanese Application No. 2011-553341, dated Nov. 29, 2013, 15 pages (with English translation).

* cited by examiner

SEALING MEANS FOR SEALING A VOLUME OF A MEDICAL TREATMENT ARRANGEMENT AGAINST ANOTHER VOLUME, AS WELL AS AN ARRANGEMENT AND A METHOD

CROSS REFERENCE TO RELATED APPLICATIONS

This is the national stage (Rule 371) of international application No. PCT/EP2010/001455 filed Mar. 9, 2010, claiming priority to German Patent Application No. 10 2009 012 632.5 filed Mar. 10, 2009.

FIELD OF THE INVENTION

The present invention relates to a sealing device for sealing at least one first volume of an arrangement for the treatment of medical fluids. It furthermore relates to an arrangement for treating medical fluids that includes a sealing device in accordance with the present invention, and a method for treating medical fluids by using the arrangement in accordance with the present invention.

BACKGROUND OF THE INVENTION

In technical arrangements such as, e.g., treatment machines of medical technology, laboratory technological arrangements, or also arrangements for the food production, functional coupling of external functional device to an arrangement is frequently envisaged. One example of such an external functional device is a disposable cassette as described in German Patent Application DE 10 2007 042 964.

Functional coupling requires an accurate connection of single components of the external functional device to components (hereinbelow also referred to as coupling mates) of the arrangement. Due to manufacturing tolerances, and/or in order to enable desired compensatory movements of single component parts during use, openings or gaps may be formed. These may be undesirable, tolerated, intended, or even necessary. Dirt particles, germs, fluids and the like may penetrate therethrough into a volume—such as, e.g., an inner space or an interior—of the arrangement, wherein this may be undesirable and may involve clearly obvious drawbacks.

SUMMARY OF THE INVENTION

It is an object of the present invention to provide another sealing device for sealing a first volume of an arrangement for the treatment of medical fluids against a second volume. Moreover it is intended to specify an arrangement for treating medical fluids including a like sealing device, as well as a method for treating medical fluids.

The object of the present invention is achieved through a sealing device having the features described herein.

The sealing device of the present invention is suitably configured and intended for sealing at least one first volume of an arrangement, in which—in accordance with its use—at least one medical fluid is treated, against at least one second volume.

Therefore, the sealing device includes at least one first connection device whereby the sealing device may be connected to the arrangement.

An "arrangement" within the meaning of the present invention preferably is a medical-technical arrangement such as, e.g., a blood treatment apparatus, for instance a dialysis apparatus. It may furthermore be an arrangement in laboratory technology, such as analytic devices, such as chromatography devices, scales and the like, an arrangement in drug manufacture, or the like. Additional examples are specified further below.

The expression "medical fluids" encompasses medical liquids such as, e.g., blood, substituate liquid, secretions and the like, without being restricted thereto.

The expression "sealing" as presently used designates the physical separation of a first volume from a second volume of the arrangement.

Sealing within the meaning of the present invention means that a sealing prevents a crossover of fluids, in particular of gas or liquids and/or of germs and/or dirt etc., from the first volume to the second volume. Preferably such sealing also encompasses the prevention of a crossover of the above-mentioned substance(s) in the above-mentioned conditions from the second into the first volume and/or in both directions at the same time.

A "first volume" may be any area within the arrangement.

The first volume may be intended for receiving at least one external functional device. The first volume preferably includes a machine interface, i.e., a coupling surface or a coupling portion of the arrangement for its functional coupling to the external functional device.

The first volume may also be an area situated at least partially outside or inside the arrangement, such as an area surrounding the arrangement, e.g., the atmosphere.

An "external functional device" may preferably transmit energy, measurement values and/or movements and forces to the arrangement or receive these from the latter. It may be in fluid communication with the arrangement. Alternatively, it may, however, also only be retained by the arrangement while not interacting and/or not being in signal communication and/or not being in fluid communication therewith.

The "external functional device" may be a heat exchanger, a measurement device, a multi-functional disposable cassette, or the like. It may include a hard part such as, e.g., a hard plastics part, and a film such as, e.g., a plastics film.

An external functional device as considered in accordance with the present invention may be suited for conducting medical fluids such as blood, substituate liquid, or the like. Such an external functional device may be, e.g., a blood-conducting cassette; it may contain parts of an extracorporeal blood circulation. In particular it may be configured as a disposable cassette as described in DE 10 2007 042 964, the entire relevant disclosure of which is hereby incorporated by way of reference. In the context of the present disclosure it may be said that the expressions "may include", "may be" and the like are synonymous with the expressions "preferably includes", "preferably is" and the like, that are used here and elsewhere.

The "second volume" may be situated in an inside of the arrangement. Functional elements of the arrangement such as, e.g., sensors and/or actuators and/or conduits and/or parts thereof may be present in the second volume.

The second volume preferably includes a reception portion for receiving the external functional device therein and/or is delimited by such a reception portion.

The second volume may be an area inside the arrangement such as, e.g., an area below an AS plate disposed so as to be capable of moving or oscillating and/or mounted so as to be capable of rotating about an axis, or below a contact portion for the external functional device.

Neither the first volume nor the second volume need to be limited or specific spaces or volumes. They may, however, be single or delimited individually, or may be spaces or encompass volumes.

A "reception portion" within the meaning of the present invention is a portion suited for receiving at least one external functional device. Receiving may denote a retaining, encircling, encompassing, covering of the external functional device and the like, as well as combinations thereof.

The reception portion, which may be—but needs not to be—flat or planar, may establish an interaction or signal communication between the external functional device and the reception portion.

The reception portion may be a reception plate such as, e.g., a preferably stable "actuator-sensor plate" (in short: "AS plate"), or the like.

The reception portion may be mounted so as to be capable of moving, oscillating, and/or rotating about at least one axis. It may thus achieve a compensation of deformations.

The reception portion may exhibit an adapted deformation capability. This may be achieved, e.g., with the aid of correspondingly selected materials. Likewise it is possible, for example, to configure the mechanism for receiving and pressing or clamping of the external functional device in or jointly with the arrangement so as to enable a deformation compensation. This may be achieved, for example, with the aid of a reception portion for receiving at least one external functional device as disclosed in the patent application the applicant of the present invention has filed at the German Patent and Trademark Office with the title "Vorrichtung zum Verbinden einer externen Funktionseinrichtung mit einer Anordnung, Anordnung aufiveisend eine solche Vorrichtung and Verfahren zum Verbinden" [Device for connecting an external functional device to an arrangement, arrangement including a like device, and method for connecting], which was deposited under the German application number DE 10 2009 012 633.3-44 for the common applicant on the same application date as the present application.

Moreover the reception portion may serve as a vacuum seal between an interior of the arrangement and the atmosphere and/or an interior of the arrangement and a treatment location in which, e.g., a treatment of medical fluids takes place. It may furthermore also be suitably configured and provided in order to enable vacuum conduction with the aid of passages provided on its surface.

An "AS plate" may include actuators and/or sensors and/or conduits for coupling to the external functional device or to parts thereof. For example, an air distribution plate and/or a substituate connector may be provided in and/or on the AS plate.

Likewise, sensors and/or actuators and/or conduits and/or parts thereof may be integrated or held in the AS plate. Furthermore all of the sensors employed in accordance with the present invention may be accommodated by the AS plate and/or positioned thereon.

A like AS plate may serve as a reception portion for positioning and fixing the external functional device. Just like any reception portion within the meaning of the present invention, it may serve as an abutment for pressing the external functional device.

A like AS plate that is mounted so as to be capable of oscillating and/or rotating about an axis may, for example, be a coupling surface as described in the patent application the applicant of the present invention has filed at the German Patent and Trademark Office with the title "Device for connecting an external functional device to an arrangement, arrangement including a like device, and method for connecting", which was deposited under the German application number DE 10 2009 012 633.3-44 for the common applicant on the same application date as the present application. The relevant disclosure of the above-identified patent application is fully incorporated herein by way of reference thereto.

The definition and/or capacity of the first and second volumes result from the construction and/or from the current condition of the arrangement. In a closed condition of the arrangement—e.g., closed by means of a door of the arrangement—, both the first volume and the second volume may be situated inside the arrangement. In an opened condition of the arrangement—e.g., when the door of the arrangement is open—the first volume may be the atmosphere or the close vicinity of the arrangement.

A "connection device" within the meaning of the present invention denotes a device that is suitably configured and provided for connecting the sealing device to the arrangement.

The first connection device may be an integral part of the sealing device. It may, however, also be a connection device that is connected to the sealing device by form closure and/or frictional connections.

The first connection device may be present on at least one portion of a side of the sealing device. It may, however, also be provided on an upper surface and/or on a lower surface of the sealing device or connected thereto.

In accordance with the present invention, each connection device may be realized of one or several connection elements.

The expression "connecting" or "establishing a connection" as presently used may denote or encompass a functional and/or mechanical connection of the external functional device to the arrangement. "Connecting" two elements to each other results in a sealing connection in the area of the connection device within the meaning of the presently employed expression of "sealing."

A suitable connection between the sealing device and the arrangement may be a frictional and/or form closure and/or material connection.

The sealing device may be connected to at least one portion of the arrangement such as, e.g., a supporting device for receiving the AS plate in an interior of the arrangement, and/or to the AS plate and/or to some other appropriate element of the arrangement.

A like "supporting device" may be a stable supporting device such as, e.g., a support frame.

The support frame may be part of the reception device for receiving the at least one external functional device.

The supporting device may be connected to the arrangement by frictional and/or form closure and/or material connection.

With the aid of the connection effected between the sealing device and a supporting device it is also possible to achieve sealing of the first volume of the arrangement against the second volume.

In a preferred embodiment of the present invention, the first connection device is configured for connection to a second connection device that is part of the arrangement in a functional or structural sense.

A "second connection device" as may be employed in accordance with the present invention may be configured in order to effect a frictional and/or form closure and/or material connection with the first connection device.

The number of elements of the second connection device may correspond to the number of elements of which the first connection device is formed. In addition, the position, i.e., the geometrical disposition of the second connection device on the arrangement may be selected such that it opposes the first connection device of the sealing device.

Geometry and/or dimensioning of the second connection device may be provided and configured in such a way that it may be combined with or connected to the first connection device in a kind of "key/lock principle." The first and the second connection device may accordingly form a connection pair. This facilitates a connection of the first connection device to the second connection device (or vice versa) and thus simplifies the connecting operation. Moreover, it may frequently be possible to achieve improved sealing. Furthermore it may be possible to easier recognize a secure connection and thus reliable sealing as well as a faulty connection or seal.

The second connection device may be connected to the arrangement via a frictional and/or form closure and/or material connection. It may form a part of the arrangement. It may also be connected to the arrangement in a releasable manner.

In another embodiment of the present invention, the first connection device may be configured for a frictional and/or form closure connection to the second connection device.

Suitable frictional connections encompass connections effected by pressure and/or friction forces. Without being restricted thereto, they encompass connections achieved through bolts, wedges, clamps and/or by using a snap-on clip.

Suitable form closure connections encompass connections effected by mutual engagement of the first and second connection device. Without being restricted thereto, they encompass releasable connections such as snap-on connections, groove-and-tongue connections, groove-and-tongue joints, dovetail joints, connections by means of feather keys, as well as non-releasable connections such as, e.g., connections effected by riveting, pins, or the use of adhesive bonds.

The first connection device may preferably be introduced into the reception device in a form-fit connection.

The first connection device may include a thickening and/or a barb or some other suitable element whereby it may be hooked in the reception device.

A like "hooking element" may be provided on the first connection device, however the first connection device may itself just as well be configured in the form of such an element. Likewise, the second connection device may be configured to include a "hooking element" or be configured as such one.

The connection between the sealing device and the arrangement may be a readily releasable connection that may be released, e.g., by merely pulling out the first connection device from the second connection device, for instance by pulling on the sealing device. It may also be a connection that can only be released by exerting considerable force.

In case several elements of the respective first and second connection device are to be connected to each other, the corresponding connection pairs may be connected to each other in a same or different manner.

In another preferred embodiment of the present invention, the first connection device is configured as an insertable device which may be inserted into the second connection device having the configuration of a reception device for the insertable device.

The first connection device may protrude at least at one rim or surface of the sealing device.

The second connection device, which forms a reception device for the first connection device, may be or may include an indent and/or a notch provided in the arrangement.

The reception device may encircle and/or encompass the insertable device.

The insertable device may preferably be inserted into the reception device in a form-fit relation. The insertable device may comprise a thickening and/or a barb or some other suitable element whereby it may be hooked in the reception device.

The insertable device may have a greater volume than the receiving volume of the reception device. It may, however, also have a smaller volume and leave a space in the reception device. In the latter case, the insertable device may be movable inside the reception device. In such a case, the sealing device may accordingly contribute to an increased relative mobility of the arrangement and sealing device or coupling surface, or AS surface, respectively.

In another preferred embodiment of the present invention, the second connection device is configured as an insertable device that is insertable in the first connection device, which in turn is configured as a reception device for the insertable device.

As such an embodiment of the present invention constitutes a reversal of the above-described embodiment, reference may be made to the preceding description for a description of the present embodiment while taking into account the exchange of first and second connection device.

In a further preferred embodiment of the present invention, the sealing device further includes a "third connection device" for connection of the sealing device to a reception portion of the arrangement or to a reception device for receiving the external functional device.

Moreover, the third connection device may be configured so as to be adapted for connection to a fourth connection device of the reception portion.

The third connection device and the fourth connection device may oppose each other on mutually facing sides of the sealing device and of the reception portion. For example, the third connection device may be provided on a lower surface of the sealing device. The fourth connection device may correspondingly be disposed on an upper surface of the reception portion.

As was set forth in the foregoing, the third connection device may be configured as an insertable device or as a reception device for an insertable device. For the description of a third connection device configured in such a way, reference is now made to the above-described embodiments.

Accordingly, the "fourth connection device" may be configured as a reception device for an insertable device or as an insertable device.

The third and the fourth connection device may correspondingly form a connection pair.

In a further preferred embodiment, at least the first connection device, the second connection device, the third connection device, and/or the fourth connection device is/are configured peripherally.

The expression "peripheral" as used herein means that the respective (first, second, third and/or fourth) connection device is configured to be continuous, i.e., not or substantially not interrupted around an area encircled by it.

The connection device may be provided peripherally on an external boundary of the sealing device. It may be provided peripherally on an internal boundary of a component of the arrangement. It may, for example, be provided peripherally on the internal boundary of the supporting device. It may just as well be provided in at least one portion of the lower surface of the sealing device. It may furthermore be provided in at least one portion of the upper surface of the reception portion in order to receive the external functional device.

In a further preferred embodiment, one or several ones of the connection device are configured as sealing lips. The sealing lips may represent an elastic seal and be realized, e.g., of metal, plastics, elastic rubber, or combinations thereof.

In a further preferred embodiment of the present invention, the first connection device together with the second connection device and/or the third connection device together with the fourth connection device are configured so as to jointly effect a respective fluid-tight seal.

The expression "fluid-tight" as used herein indicates that the penetration of any fluid and/or the penetration of a component by any fluid, for example a medical fluid such as blood, substituate liquid or the like, is substantially prevented.

A fluid-tight seal preferably also prevents the penetration of gases such as, e.g., air from the first volume into the second volume, or vice versa.

In a further preferred embodiment, the first connection device has in at least one portion thereof a lower thickness than another portion of the sealing device.

Owing to a lower thickness, such a portion of the first connection device may be realized to have a higher flexibility while using the same material. The sealing device may accordingly be configured to be movable.

The portion having a lower thickness may be disposed in the vicinity of the first connection device and/or between the first and third connection device. It may furthermore be the one portion of the sealing device covering a free space between the reception portion for receiving an external functional device and the supporting device.

For example, the sealing device includes—preferably between two peripheral sealing lips—a peripheral area of the sealing device having a lower thickness. A sealing device configured in such a way may yield locally—for example during an operation of coupling an external functional device to the arrangement—to a movement of the reception portion in the area of lower thickness of the sealing device. Such an area of lower thickness may, for example, be an area disposed in an immediate vicinity of the opening or gap between the reception portion and the supporting device. Such a lower thickness may advantageously admit, e.g., pivoting of the sealing device or of an area thereof, in particular of a boundary area, for example through three degrees relative to a main extension or extension at rest.

In a further preferred embodiment of the present invention, the sealing device covers at least one portion of a surface of the reception portion for receiving the external functional device.

Such a "surface of the reception portion" may be the surface facing the external functional device. It may be the side on which the external functional device rests.

The sealing device may cover the surface of the reception portion in a boundary area or in several boundary areas of the reception portion. It may expose an internal area or a central area of the reception portion. The sealing device may cover the reception portion in predetermined areas.

In a further preferred embodiment, the sealing device in its condition of use covers the entire surface of the reception portion. Here, the surface, in the scope of the present invention, may be understood as to be the surface facing the external functional device, i.e. for example the surface on which the external functional device rests.

The sealing device may, e.g., span the movably mounted AS plate or coupling surface of the external functional device and at the same time span and seal the gap or opening between the movably mounted AS plate and the surrounding stationary supporting device such as, e.g., a machine frame.

The sealing device may cover the surface of the reception portion in a regular manner. It may have a thickness that is the same in each area. It may further include areas of greater or lower thickness.

In a further preferred embodiment of the present invention, the sealing device is configured and provided so as to be adapted for frictional and/or form closure connection to a reception portion of the apparatus for receiving the external functional device.

The sealing device may be adapted for connection to the reception portion, e.g. by mutual combination, in particular mutual insertion, of the third connection device and the fourth connection device. It may further be snapped onto the reception portion. A snapped-on sealing device may advantageously be removed, i.e., taken from the reception portion in a quick, simple and easily releasable manner.

In another preferred embodiment of the present invention, the third connection device or the fourth connection device includes at least one knob.

A "knob" within the meaning of the present invention designates a protuberance at the surface of the third or fourth connection device. The third or fourth connection device, in turn, may itself have the form of a knob.

A knob is preferably formed of rubber.

A knob may represent an easily formed connection device. The knob may in addition represent a connection that may easily and quickly be released.

In a further preferred embodiment of the present invention, the sealing device is configured so as to be connectable to the surface of the reception portion by the application of negative pressure.

Such a negative pressure may be generated, e.g., by sucking the sealing device in a direction toward the surface of the reception portion through openings in the sealing device and/or in the reception portion and/or by evacuating an interstice between the sealing device and the reception portion.

In order to evacuate the interstice between the sealing device and the reception portion, air passages may be provided which are not covered or obstructed by the sealing device. In this way a reliable conduction of air may be ensured.

Moreover an air-conducting intermediate layer such as, e.g., a nonwoven material may equally be provided, and/or a sufficient number of vacuum feed locations may be formed in the reception portion.

By the application of negative pressure for the purpose of connecting the sealing device to the surface of the reception portion, the sealing device may be connected to the reception portion in a releasable manner.

In a further preferred embodiment, the sealing device may be configured for a non-releasable connection to the arrangement.

Such a non-releasable connection between the sealing device and the arrangement may be achieved by bonding the sealing device to the arrangement, vulcanizing the sealing device onto the arrangement, soldering at least one portion of the sealing device to the arrangement, or in a variety of other ways.

Whenever a non-releasable connection is mentioned in the context of the present invention, this may be understood as to be a sealing device which cannot be removed, i.e., detached or taken off from the support surface or from the reception portion, e.g., from the AS plate, without any destruction.

A non-releasable connection of the sealing device to the arrangement may, e.g., also be realized as a so-called "tamper evidence closure." A like tamper evidence closure may be provided, e.g., on the outer sealing lip. It may, for instance, serve to prevent an attempt to remove the sealing device or to indicate such an attempt if it should have taken place. Any faulty seal, or a seal that is not secure any more, may thus advantageously be recognized in a quick and safe manner.

To this end, the seal in the sealing groove of the supporting device may tear upon its removal to thus render the sealing device unusable.

The sealing device may be connected with the reception portion in a non-releasable manner, e.g., in the form of an actuator-sensor plate, and/or with the frame provided by the arrangement or a different portion hereof. In such embodiments, it is not possible to remove or detach the sealing device from the reception portion in a non-destructive way and/or without special tools which, e.g., usually are only available to the service technician.

In certain embodiments of the present invention, the sealing device may be hooked, e.g., for the purpose of the tamper-evident closure, by means of mechanical elements such as hooks from behind, i.e. from the machine side. Respective hooks may be provided, e.g., in a section of the reception portion. For receiving the hooks, the sealing device may comprise, for example, a peripheral lip (with a width of, e.g., 10 mm) on its back. In such embodiments, apertures for hooking the hooks may be provided. These hooks may, e.g., be removable in a non-destructive way only by means of special tools by the service technician. Hooks are only one example for an—in particular mechanical—restraint system. It may be arbitrarily embodied.

In a further preferred embodiment, the sealing device includes in at least one portion predeformed areas which are configured by weakened areas or reinforcements as compared with a thickness of those areas of the sealing device surrounding the predeformed areas.

The sealing device itself may serve as a sensor and/or actuator. This may be achieved, e.g., by realization of the above-mentioned predeformed areas.

Predeformed areas of the sealing device may fulfil, e.g., a sensor function for recognizing the presence of the external functional device.

By way of example it may be desirable to achieve a fluidic separation of passages in the external functional device by pressing or raising a film of the external functional device against the hard part or body of the external functional device. This may, for example, be obtained by means of a force that is conveyed by the sealing device and/or an actuator entirely or partially contained in the sealing device and/or an actuator provided or integrated on an AS plate of the arrangement. On the other hand, such passages may also be interconnected by raising or pressing the film.

To this end, the sealing device may include passage openings disposed either permanently at supply points, for example for substitute liquid, and/or variably at supply points such as substituate conduits. For this purpose, the sealing device may furthermore include Single-Needle (SN) chamber openings.

The forces required for pressing or raising the film may be transmitted to the film, e.g., through the intermediary of the sealing device.

In a further preferred embodiment of the present invention, the predeformed areas are configured so as to fulfil a valve function.

A valve function may be effected, e.g., by a phantom valve actuator as described in the following. The latter may preferably be configured as a complete piston seal.

The phantom valve actuator may be configured as diaphragm actuators jointly integrated into a sealing mat. The sealing mat may be configured as an air distribution plate (in short: LVP; LuftVerteilerPlatte).

The actuator diaphragm integrated into the LVP sealing mat may be configured to expand under pressure and push a tappet in a direction toward a surface of the sealing device which contacts or opposes the external functional device.

Such a tappet may be operated electrically, pneumatically and/or hydraulically.

The tappet may include a piston seal or act as a piston seal.

The tappet may be provided on the AS plate and/or integrated therein.

The tappet may be suitably configured and provided so as to push against the sealing device and thus against the film of the external functional device.

The tappet may likewise be suitably configured and provided so as to raise the sealing device from the film. This may be achieved, e.g., as a result of its connection to the AS plate such as, e.g., a connection by bonding, vulcanization, application of negative pressure, and the like. The film may then detach itself from the hard part of the external functional device.

Moreover, such a function may be assisted by the predeformed areas provided in the sealing device and the resetting forces of an elastic sealing device.

In certain embodiments, the sealing device according to the present invention is construed and provided to be able to act upon a valve device of an external functional device such that the valve device automatically and/or preferably without further action just by uniting the sealing device and the valve device may be passed into a state of use during coupling.

The valve device may be, e.g., a valve device of an external functional device such as described, e.g., in the German patent application DE 10 2009 024 469.7-44, which the applicant of the present invention has filed with the German Patent and Trademark Office, the respective disclosure of which is fully incorporated herein by way of reference thereto. The external functional device may be taken from, e.g., the German patent applications DE 10 2009 018 664.6 and DE 10 2009 024 468.9-41, which the applicant of the present invention has filed at the German Patent and Trademark Office, the respective disclosures of which are fully incorporated herein by way of reference thereto.

A valve core of a valve device, e.g., of a multifunctional valve as described in German patent application DE 10 2009 024 469.7-44, is normally—while the external functional device is being sterilized—in a position in which the valve core is not completely pressed up to the stop into the hard part of an external functional device which is, e.g., embodied as a disposable cassette.

In certain embodiments according to the present invention, a sterilizing medium, e.g., superheated steam, gas, e.g., ethylene oxide (EO), may in this position penetrate into the interior of the external functional device.

In some embodiments according to the present invention, the valve device of the fully sterilized and packaged external functional device in general remains in this state also in the delivery state to the client.

Coupling the external functional device to the arrangement may take place, e.g., with the aid of a machine door as disclosed, e.g., in the German patent application DE 10 2009 012 633.3-44, which the applicant of the present invention has filed with the German Patent and Trademark Office.

While the external functional device is being coupled to the arrangement for its use, in certain embodiments according to the present invention, the valve core is automatically pressed into the valve housing (e.g., the hard part of the disposable cassette) up to the stop by means of an elevation or a protrusion or the like on or at the surface of the sealing device.

This way, in some embodiments according to the present invention, e.g., the function of the valve device as check valve may be activated, in particular when uniting the valve device and the sealing device.

The elevation on the surface of the sealing device may be or may have been designed or effected during production, e.g., as a knob (material elevation or bulge).

For the purpose of cleaning the sealing device at a hospital, it may advantageously alternatively and/or additionally hereto be considered to provide an elevation such as a bolt, e.g., a metal bolt, in the reception portion, e.g., in a position exactly opposite to the valve device of the external functional device to be coupled.

Such a bolt or such an elevation may be a metal bolt which protrudes over or beyond the coupling surface of the reception portion. It may be pressed or screwed into the reception portion. In a non-coupled state, the bolt may lift the sealing device basically locally, preferably by a defined amount, e.g. 1 mm in a maximum of the elevation, from the reception portion or it may have it protrude accordingly.

It may thus be advantageously possible to initially keep the surface of the sealing device smooth or even and easily to clean.

When the external functional device is coupled to the sealing device, however, the bolt of the reception portion may push against the sealing device locally, it may locally buckle it in the direction towards the external functional device and thus dent the valve core, possibly up to the stop into the hard part of the external functional device.

During the coupled state of the external functional device, the sealing device may remain in the locally buckled or protruding state.

Securing the bolt by screwing, e.g., by means of a fine thread, may advantageously allow for a defined setting of the desired displacement path of the valve core.

The bolt may comprise a broadened valve support, the diameter of which is larger than the fine thread or the push-fit peg.

In a further preferred embodiment, the sealing device is configured for functional coupling of at least one external functional device.

The expression "coupling" as used herein may denote or encompass a functional and/or mechanical connection of the external functional device to a coupling mate on the side of the arrangement including an interaction and/or signal communication and/or fluid communication between external functional device and arrangement in the coupled condition of the external functional device.

A "coupling mate of the arrangement" may, for example, be a measurement device such as, e.g., a sensor. It may be a fluid conduit and the like.

The external functional device may be a cassette system. It may be suited for use in a hemodialysis method. A like cassette system may consist of a solid, three-dimensional cassette body of plastics or of some other hard material. It may be open towards one side and include numerous connection openings for the insertion or bonding and/or welding of inserted tubes.

On the open side of such a cassette body a film such as, e.g., a plastics film may be applied. The film may, e.g., be applied by bonding and/or welding. By using such a film it is possible for the cassette body and the film to form passages and chambers through which fluids such as, e.g., blood and/or substituate liquid may be conducted.

The film may be fastened to only an external boundary at the cassette body and/or to all passage delimitations. It may be desirable and advantageous not to fasten the film in certain locations that are provided for areas to be open during operation of the arrangement, in order to perform and/or ensure a valve function.

Tubes such as, e.g., plastic tubes may be fastened to connection openings of the cassette body, so that fluids may be supplied to the passages provided with the openings and/or discharged from them.

Due to the construction of the cassette including a massive cassette body on the one hand and a flexible film on the other hand, it may be possible to functionally couple various sensors for the detection of different measurement quantities in the passages and chambers and/or actuators for influencing the liquid flows of the passages to the film.

Functional coupling of the external functional device to the arrangement may suitably be achieved by mechanical coupling such as, e.g., by pressing the AS plate of the arrangement with the external functional device.

In particular this may mean that the film of the external functional device is brought into physical contact with the sealing device and is in surface contact therewith.

As the direct contact of the materials of sealing device and film may result in measuring inaccuracies, the materials are in a preferred embodiment preferably selected so as to advantageously reduce the coefficient of friction. This may be achieved, e.g., by a subsequent coating or surface modification of the sealing device. In this way, it is possible to prevent shear stresses from being passed on, e.g., to a pressure sensor.

In addition, pressing or clamping of the external functional device toward the film may be necessary in order to ensure the sealed condition of the passages of the external functional device at least in partial areas. This may be achieved by pressing the film against or onto the external functional device. Moreover it is thereby possible to support the fluidic internal pressure of the external functional device.

In order to functionally couple the external functional device to the arrangement, the latter may initially be positioned and in a given case be fixed on the AS plate and subsequently be pressed with the latter. In this way the sensors and/or actuators and/or parts thereof provided and/or mounted in and/or at the AS plate may couple to the external functional device and in particular to the film thereof. Here just like in other embodiments, elastic sealing device such as, e.g., an elastic mat of silicone may serve as a coupling mate.

Just like coupling of the sealing device to the AS plate and/or components thereof, the sealing device may also be coupled to the film of the external functional device by applying a negative pressure. In this regard, reference may also be made to the same applicant's German patent application DE 10 2007 042 964, the relevant disclosure of which is hereby fully incorporated by way of reference thereto.

Air-free coupling of the sealing device to the film of the external functional device may, however, also be effected without active evacuation of the interstice between the sealing device and the film. For example, the external functional device and the sealing device may be taken into air-free pressurized contact due to their geometrical shape. In this way they may be pressed in an appropriate manner.

Correct coupling and even a leakage of air or liquids such as, e.g., blood and/or substituate into the interstice between the sealing device and the film of the external functional device may be detected with the aid of a sensor. In this regard, reference may also be made to the applicant's German patent application DE 10 2008 062 037, the relevant contents of which are also incorporated in the present disclosure by way of reference thereto.

The sealing device may be configured and provided in a suitable manner so as to act as a diaphragm owing to its elasticity. It may suitably deform and/or propagate forces toward a sensor due to the pressure difference between the upper surface and the lower side of the diaphragm or of the sealing device. Such a sensor may be provided on the external functional device and/or on the AS plate.

The sensors and/or actuators of the sealing device of the present invention may be adapted and provided in a suitable manner for being connected to the AS plate.

In a further preferred embodiment of the present invention it is intended that the sealing device includes at least one sensor and/or actuator and/or a conduit and/or at least a part thereof.

"Sensors" as presently denoted encompass—again without being restricted thereto—electrical, optical, acoustic, mechanical, chemical, virtual and/or digital sensors, transducers and/or probes and the like.

It is, for example, possible to use a switch for a mechanical sensor. Chemical sensors may, for example, be used whenever a mat or film is permeable to gas diffusion and it is desired to measure such a diffusion of a gas.

The expression "virtual sensor" may be understood to be a sensor realized with the aid of software or an obtained effect of such a sensor, which "measures" values derived from the measurement values of real sensors with the aid of an empirically learned or physical model. Virtual sensors are preferably suited for applications in which real sensors are too costly, or in environments in which real sensors cannot endure or wear prematurely.

A sensor may qualitatively or quantitatively detect particular physical and/or chemical properties or a change thereof, such as an increase or a decrease of an effect, of a characteristic, quality and the like such as, e.g., temperature, pressure, humidity, optical signals such as, e.g., brightness and/or an optical change of a composition, heat radiation, sound, flow rates, and/or the material quality of its environment.

Sensors within the meaning of the present invention may be configured as passive sensors or active sensors.

Sensors within the meaning of the present invention may, e.g., be pressure sensors which also sense pressures lower than the environmental pressure.

Sensors within the meaning of the present invention may be pressure sensors, level sensors, optical sensors, ultrasound sensors, temperature sensors, and the like more.

Sensors within the meaning of the present invention may be capacitive sensors that detect the fluid level, in particular the liquid level, in the chambers formed by the hard part of the external functional device and the film of the external functional device. Suitable capacitive sensors may detect dielectricity differentials through the sealing device.

In a preferred embodiment, the sealing device of the present invention includes at least one thinning. The thinning may be configured so as to assist check valves. It may have a lower resilience than other areas. It may have a depth of 0.5 to 1 mm, for example.

The thinning may be provided above a pressure sensor.

The thinning may serve for reducing the influences of pressing on the pressure measurement.

The sealing device may include at least one pre-form for valves or chamber conduits.

The sealing device may include at least one recess. The recess may be configured for a permanent passage opening. It may have a depth of, e.g., 1 mm.

The sealing device preferably includes a pre-form for a post-dilution valve. It preferably includes a pre-form for an SN valve (Single-Needle valve). It preferably includes a pre-form for a pre-dilution valve.

The sealing device preferably includes a fastening device for fastening an external functional device thereto. The fastening device may be a positioning pin.

The sealing device preferably includes a substituate connector. The latter may be an automatic substituate connector.

The sealing device preferably includes a free position for introducing a vacuum and/or for evacuating the film of the disposable cassette.

The reception portion may be part of a blood treatment apparatus.

The fourth connection device of the reception portion may be a notch for receiving the third connection device that is configured as a sealing lip. The sealing lip of the sealing device and the notch of the reception portion may jointly form a vacuum seal.

The reception portion preferably includes supports for check valves.

The reception portion and/or the sealing device may include various valves, e.g., a post-dilution valve, an SN valve and/or a pre-dilution valve. The post-dilution valve and the pre-dilution valve may each have a diameter of 5 mm to 25 mm, preferably 9 mm. The SN valve may have a diameter of 5 mm to 40 mm, preferably 18 mm.

The reception portion and/or the sealing device may include various sensors. These exemplarily cover an SN pressure sensor, an SN level detector, a level detector, for example for detecting the blood level of a venous chamber, sensors for detecting the coupled external functional device, a venous pressure sensor, an arterial pressure sensor, a coupling sensor, and/or a pre-filter pressure sensor.

The SN pressure sensor may preferably detect both a pressure above atmospheric and a negative pressure, preferably from −333 mbar to +1000 mbar, in a particularly preferred manner from −266 mbar to +800 mbar.

The venous pressure sensor may preferably detect both a pressure above atmospheric and a negative pressure from −333 mbar to +1000 mbar. The venous pressure sensor may preferably detect both a pressure above atmospheric pressure and also a negative pressure, preferably from −266 mbar to +800 mbar.

The arterial pressure sensor may preferably detect both a pressure above atmospheric and a negative pressure from −733 mbar to +600 mbar, in a particularly preferred manner from −533 mbar to +533 mbar.

The pre-filter pressure sensor may preferably detect a pressure (negative pressure and pressure above atmospheric) from −133 mbar to +2868 mbar. The pre-filter pressure sensor may preferably detect a pressure of up to +1500 mbar.

The reception portion preferably includes an evacuation opening for evacuating air from between the reception portion and the sealing device. The evacuation opening may be suited for generating a negative pressure from −680 mbar to −700 mbar. The evacuation opening may be suited for generating a negative pressure corresponding at least to the lowest negative pressure to be measured, preferably from −500 mbar to −800 mbar.

The evacuation opening may be suited for generating a negative pressure from preferably −500 mbar to −800 mbar.

The sealing device preferably includes a plunger for the coupling sensor. The coupling sensor may be an optical sensor. The plunger may be movable. The plunger may be moved by means of pressing force.

The sealing device preferably includes a plunger for the sensor for detecting or recognizing the coupled external functional device. The plunger may be movable by the application of pressure.

The sensor for detecting the coupled external functional device may be realized to have the same construction as the coupling sensor.

The sealing device may include a pressure pad for the pressure sensor. The thinning above the pressure sensor may preferably amount to 0.1 mm to 1.5 mm, in a particularly preferred manner 0.5 mm. These values may designate a relative thinning in the sense of a thinning as compared to an area that is not thinned. They may alternatively be understood to be absolute values, i.e., geometrical indications for the thickness or amount of the thinning.

The external functional device preferably includes a cavity for a check valve. The check valve may be formed of silicone, for example.

"Actuators" in the presently used sense include—without being restricted thereto—mechanical and/or pneumatic and/or electrical components such as, e.g., valves, positioning and/or regulating members, motor operators, pressure pistons, and the like.

Conduits as may be used in accordance with the present invention may include—without being restricted thereto—fluid conduits such as, e.g., blood-conducting passages, substitute conduits, electrical lines, lines for signal communication such as, e.g., glass fiber cables, and the like.

In a further preferred embodiment of the present invention, sensors and/or actuators and/or conduits and/or parts thereof are connected to the sealing device by form closure and/or frictional and/or material connections.

A suitable connection may be achieved, e.g., by directly integrating the sensors and/or actuators and/or lines and/or parts thereof into the sealing device. For example, sensors and/or parts thereof may be cast with the sealing device and/or vulcanized into it. Hereby, it may advantageously be achieved that the measured distance between the sensor and the sealing device is reduced by the coupling location of the sensor in the sealing device.

In a further preferred embodiment of the present invention, the sealing device includes at least one reception for a fastening device of the external functional device and/or of the reception portion.

A "fastening device" as suitably used and provided herein may be at least one element selected from among a group of elements such as positioning pins, substituate connectors, positioning mandrels, bolts, brackets, wedges and the like.

A "reception" for such a fastening device may be an opening provided in the sealing device, a through hole, an opening, a slot, a gap, a hole or the like.

Combining the fastening device with the reception, in particular the introduction of the fastening device into the reception and/or, in a given case, fixation of the fastening device in the reception, may serve for positioning and/or fixation of the external functional device and/or of the AS plate.

The areas provided for receiving such fastening device are preferably disposed outside the blood-conducting areas of the external functional device.

In a further preferred embodiment, the sealing device is configured as a multi-component sealing device or comprises such a material.

In a further preferred manner, the sealing device may include at least one elastomer material or be comprised thereof. A suitable elastomer material may examplarily be—without being restricted thereto—rubber, silicone, caoutchouc, plastics, PVC and the like.

A suitable elastomer material may furthermore include liquid-crystalline elastomers and/or thermoplastic elastomers.

Such multi-component sealing device may be obtained, e.g., by injection-molding an elastomer material around hard parts such as, e.g., plastic parts, and/or snapping or bonding these hard parts into an elastomer part. In this way, a stable structure of the sealing device may be formed which has components that are stable themselves.

As an alternative, the sealing device may be formed in its entirety of the elastomer material, whereby easy manufacture and lower production costs may advantageously be realized.

The sealing device may be a dimensionally stable, elastic or resilient or flexible and/or mobile or movable sealing device. The sealing device may be configured, e.g., as a mat, for example, as a machine mat.

The sealing device of the present invention may be configured such that it will not substantially influence the propagation of an electric field. It may be configured to be electrically insulating. It may be configured with sufficient sensitivity to also sense and/or convey, e.g., a low pressure in the arrangement and/or in the external functional device.

The sealing device may have a thickness of 1.0 mm to 10.0 mm, preferably of 2.6 mm.

In a further preferred embodiment, the sealing device may be configured to have a greater thickness (e.g., a thickness of 2.6 mm) in the areas of pressing, however, in the areas of chambers, level detectors, channel outer areas, check valves and the like with a lower thickness (e.g., a thickness of 0.1 mm to 1.5 mm, preferably 1.0 mm). In areas of pressure sensors, the sealing device may have a thickness, e.g., of 0.5 mm. It may have a Shore hardness of 30° to 80°, preferably of about 50°.

In another embodiment, a pressing force for pressing the external functional device to the reception portion in the center axes of the reception portion of 0.5 kN to 10 kN, preferably of about 5 kN, is employed. Substitute valves apply a required force of about 5 N to 50 N, preferably about 40 N. The force of the SN valve is 20 N to 200 N, preferably 100 N.

In one embodiment of the sealing device of the present invention, a possible passage seal of the sealing device that is possible in accordance with the present invention is modified such that pressing is only required at the valves. In this way the pressing force may be reduced clearly (in a preferred manner below about 2.5 kN). This advantageously allows the possibilities of optimization, e.g., with regard to thickness, geometry and choice of material, in the area of the sealing device. It is thus advantageously also possible to further optimize the interaction of sealing device and reception portion.

In a preferred embodiment, the arrangement is configured as an arrangement for treating medical fluids. In particular, the arrangement of the present invention may be configured as a dialysis apparatus, a hemodialysis apparatus, an apparatus for hemofiltration or for hemodiafiltration, and the like.

The arrangement of the present invention may be configured as an arrangement in laboratory technology such as, e.g., an analytic apparatus such as a chromatography apparatus, scales and the like, and/or as an arrangement in the production of food and/or drugs.

In a preferred embodiment the arrangement of the present invention includes a negative pressure device for fixing the sealing device to the arrangement by means of negative pressure.

The method relates to a treatment of medical fluids and includes the use of an arrangement in accordance with the present invention.

For the sole purpose of avoiding repetitions, reference is here expressly made to the embodiments described in the foregoing, and to the advantages mentioned hereinbelow which apply for any embodiments of the method of the present invention and of the arrangement of the present invention and may be obtained undiminishedly therewith.

The sealing device of the present invention is advantageously suited for sealing at least one first volume of an arrangement for the treatment of at least one medical fluid against at least one second volume of the arrangement. It may advantageously furnish sealing of the passages for conducting fluids that are provided in an external functional device.

The sealing device of the present invention may advantageously provide a vacuum seal. The sealing device of the present invention may advantageously support the film of an external functional device and/or its evacuation.

As the sealing device of the present invention may be formed of an elastic—preferably elastomer—material and/or may include such one, it may itself advantageously function as a sensor in at least one portion or represent part of a sensor. To this end, it may effect, e.g., passing on pressure and/or conveying pressure. Owing to the quality of its material, however, it may also effect pressure insulation. By means of a mechanical deformation of the sealing device, the latter may advantageously allow for a comparative pressure measurement, for example by connecting a coupling sensor.

The sealing device of the present invention may advantageously also allow for passing on and/or insulation of temperatures, electrical voltages, and electrical currents.

Particularly if the sealing device of the present invention includes an elastomer material, it may moreover admit a tilting movement of the reception portion for receiving the external functional device on the arrangement. Owing to its material properties, it may furthermore admit a compensation of tolerances between the different components of the arrangement and/or of the external functional device, in particular of a hard part of the external functional device.

Owing to the flexibility and/or mobility or movability of an elastomer sealing device, it may advantageously also be possible to compensate manufacturing tolerances and connection transitions in the area of valves.

As the sealing device of the present invention may have elastic properties and protrude beyond the AS plate and may be connected to adjacent housing parts, for example to the supporting device such as a machine frame or support frame, it is advantageously possible to realize a smooth machine surface that may easily be cleaned.

In addition—and furthermore favored by the method of manufacturing the sealing device or by its dimensions—it is advantageously possible to avoid the occurrence of undercuts that are difficult to clean.

In a given case, it may moreover advantageously be possible to also reliably bridge and seal large gaps and/or openings, which may be required in order to realize component parts having relative mobility, wherein it is possible to avoid an inhibition or restraint of their mobility or movability. In particular, this may advantageously be favored by the areas of the sealing device having a lower thickness that are provided in the first connection device.

In particular when the sealing device of the present invention has a closed configuration—i.e., without through holes or areas remaining free in an inner area thereof—it is advantageously possible to protect all of the components disposed under the sealing device in a highest possible degree against mechanical, electric, chemical and/or radiation influences.

When the sealing device of the present invention is configured as a sealing device that is open in an interior thereof, it is advantageously possible to directly couple selected sensors to the film of the external functional device. As the sealing device of the present invention is well suited for fastening, e.g., to the AS plate and capable of sealing the open area against areas of the AS plate that are covered by the sealing device, the surface of the AS plate may also be easy to clean in the case of an open sealing device.

The sealing device of the present invention has a high suitability for functional integration. In particular, it is advantageously possible to integrate functions required for the operation of a blood treatment apparatus, such as a dialysis machine, while interacting with the external functional device such as a disposable cassette, in the sealing device of the present invention.

In the present sealing device, the impairments of measurement accuracy caused by the sealing device of the present invention and by the film of the external functional device, as well as those caused by the direct contact of the materials, may advantageously be reduced by various measures. It may thus, for example, advantageously be possible to clearly reduce the thickness of the sealing device in the area of the sensors and/or to lower the coefficient of friction of the material partners (for instance: sealing device and external functional device).

In addition, the sealing device of the present invention may advantageously detect the presence of an external functional device with the aid of a coupling sensor, in particular in the presence of a mechanical resetting force that is constant due to geometry and/or material. Such coupling sensors may be provided in the reception portion.

A preferably provided IR opacity of the sealing device may equally contribute to the recognition of an external functional device.

When a pressure within the passages and/or chambers of the external functional device is to be detected, it is advantageously also possible—due to the pressure conduction properties of a sealing device formed and provided, e.g., of elastomer—to dispose and/or fix the sensors in a protected manner inside the sealing device in the AS plate. The sealing device of the present invention may thus advantageously represent a protective function for sensors and/or actuators and/or conduits against external influences. This may result in a protection for the sensors and moreover enhanced accuracy of the values measured by means of the respective sensors.

It may be particularly advantageous as the sealing device is capable of ensuring secure sealing of the interstice between the film of the external functional device and the sealing device against leakage air from outside. This may be effected by providing a sealing lip at the sealing device.

When the sealing device of the present invention is connected to a support surface such as the AS plate with the aid of negative pressure, the sealing device may advantageously be released easily from the AS plate and/or other components following cancellation of the negative pressure. In this way a replacement of the sealing device due to damage and/or aging or its removal for cleaning purposes may advantageously take place in an easy manner.

The tamper evidence closure that may be realized in accordance with the present invention may advantageously prevent improper assembly or disassembly of the sealing device. Moreover, it may advantageously prevent a transmission of germs. In addition it is possible to obtain a surface that is well suited for cleaning. As the gap or opening is not accessible to the user in this embodiment, a penetration of undesirable particles such as dust, and/or of fluids such as substituate liquid and/or blood, may advantageously be avoided or even prevented in a particularly reliable manner.

When the sealing device is configured as a multi-component sealing device, certain portions of the sealing device may advantageously be configured, intentionally and independently of each other, for positioning, fastening, deformation and under aspects of an enhanced service life.

BRIEF DESCRIPTION OF THE DRAWINGS

In the following, the sealing device of the present invention shall be described by way of preferred embodiments thereof while making reference to the figures. In the drawing same reference numerals designate same or identical elements, wherein:

FIG. 7 schematically shows a snap connection of the sealing device of the present invention in cross-sectional view, with the sealing device not being snapped on.

FIG. 8 schematically shows a snap connection of the sealing device of the present invention in a cross-sectional view, with the sealing device being snapped on.

DETAILED DESCRIPTION OF THE DRAWINGS

Figure 1:
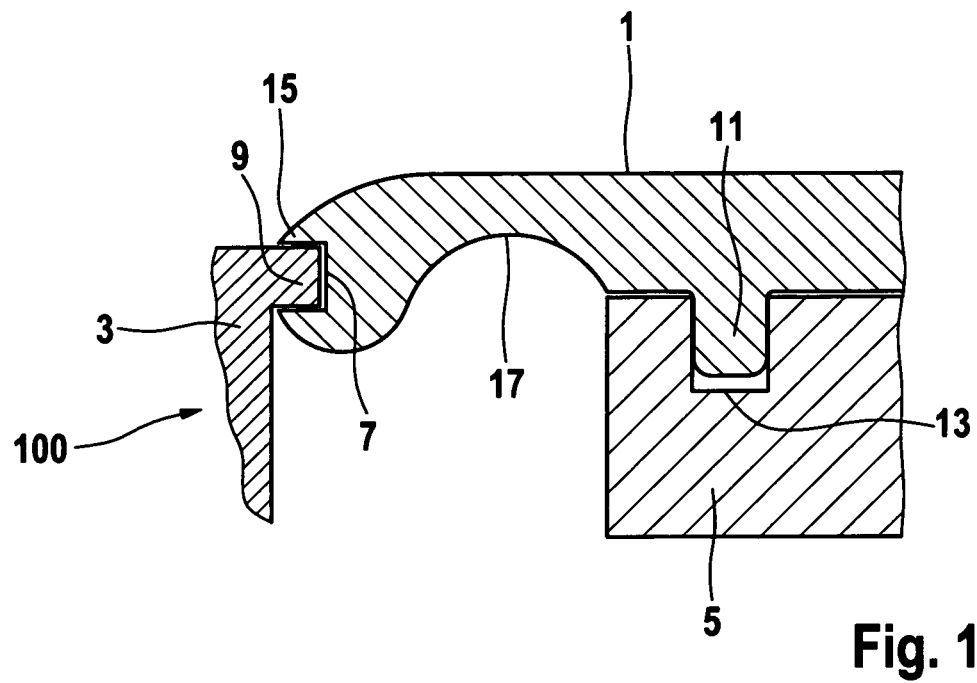
FIG. 1 shows a partial sectional view in a lateral area of a sealing device in accordance with a first embodiment of the present invention that is connected to an arrangement.

FIG. 1 shows a cross-sectional view of a portion of a sealing device 1 in accordance with a first embodiment of the present invention, that is connected to a supporting device 3 of an arrangement 100 and to a reception portion 5 of the arrangement 100. The arrangement 100 may be a blood treatment apparatus. The supporting device 3 of the arrangement 100 may be a support frame. The reception portion 5 of the arrangement 100 may be an AS plate.

The sealing device 1 includes a first connection device 7. The first connection device 7 is a reception device for an insertable device. The supporting device 3 includes a second connection device 9. The second connection device 9 is an insertable device.

The sealing device 1 includes a third connection device 11. The third connection device 11 again is an insertable device. The reception portion 5 includes a fourth connection device 13. The fourth connection device 13 is a reception device for the third connection device 11 of the sealing device 1 that is configured as an insertable device.

The sealing device 1 includes a projecting lip 15 for the transition to the supporting device 3.

In the area of the first connection device 7, the sealing device 1 includes an area 17 having a lower thickness in comparison with other portions of the sealing device 1.

Figure 2:
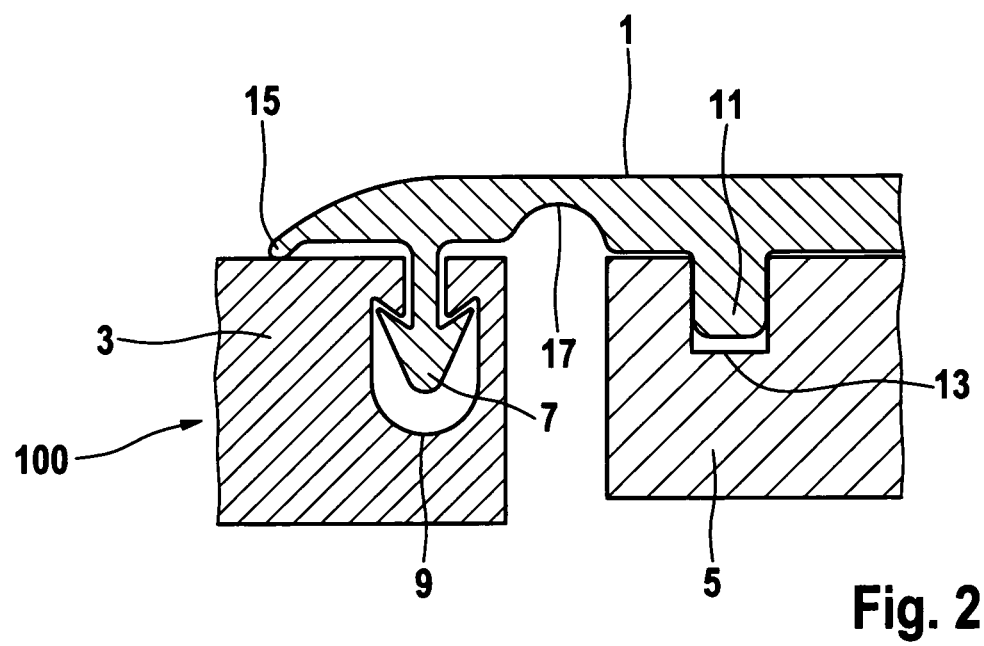
FIG. 2 shows a partial sectional view in a lateral area of a sealing device in accordance with a second embodiment of the present invention that is connected to an arrangement.

FIG. 2 shows a cross-sectional view of a portion of a sealing device 1 in accordance with a second embodiment of the present invention.

The sealing device 1 of the second embodiment substantially corresponds to the one of the first embodiment. It does, however, differ from that of FIG. 1 in that the first connection device 7 of the sealing device 1 is configured as an insertable device, and the second connection device 9 of the supporting device 3 is configured as a reception device for the first connection device 7.

In the second embodiment of FIG. 2, the first connection device 7 is a barb.

Figure 3:
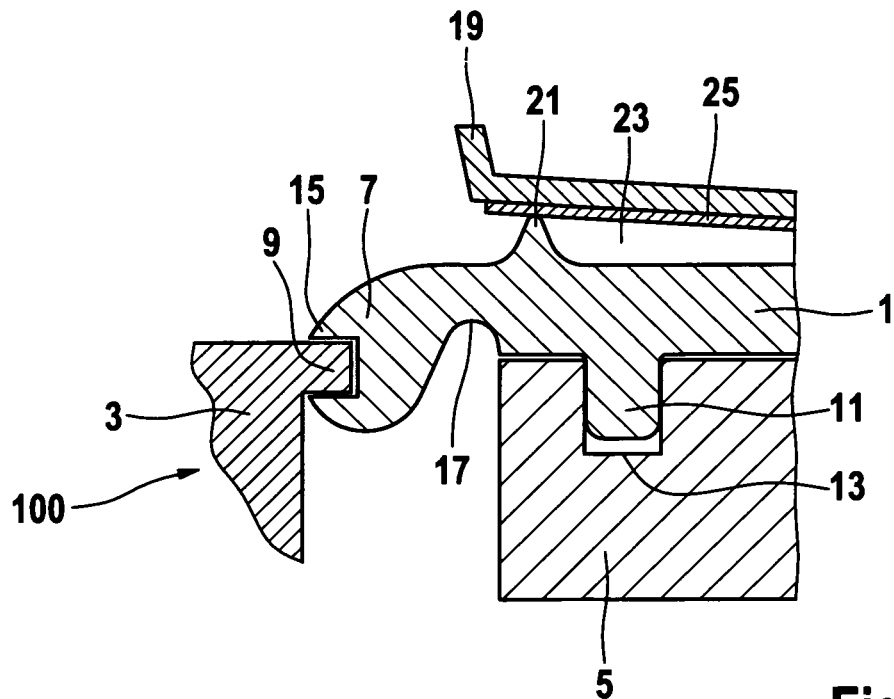
FIG. 3 shows a partial sectional view in a lateral area of a sealing device in accordance with a third embodiment of the present invention that is connected to the arrangement and to an external functional device.

FIG. 3 shows a cross-sectional view in a lateral area of a sealing device 1 in accordance with a third embodiment of the present invention. The sealing device 1 is connected to the arrangement 100 and to an external functional device 19. The external functional device 19 may be a blood-conducting disposable cassette.

The sealing device 1 includes a vacuum seal 21 for sealing an interstice 23 between a film 25 of the external functional device 19 and the sealing device 1. The vacuum seal 21 contacts the film 25. The vacuum seal 21 may be configured as a sealing lip.

The interstice 23 may be evacuated in order to connect the external functional device 19 to the sealing device 1 and functionally couple the external functional device 19 to the arrangement 100.

Figure 4:
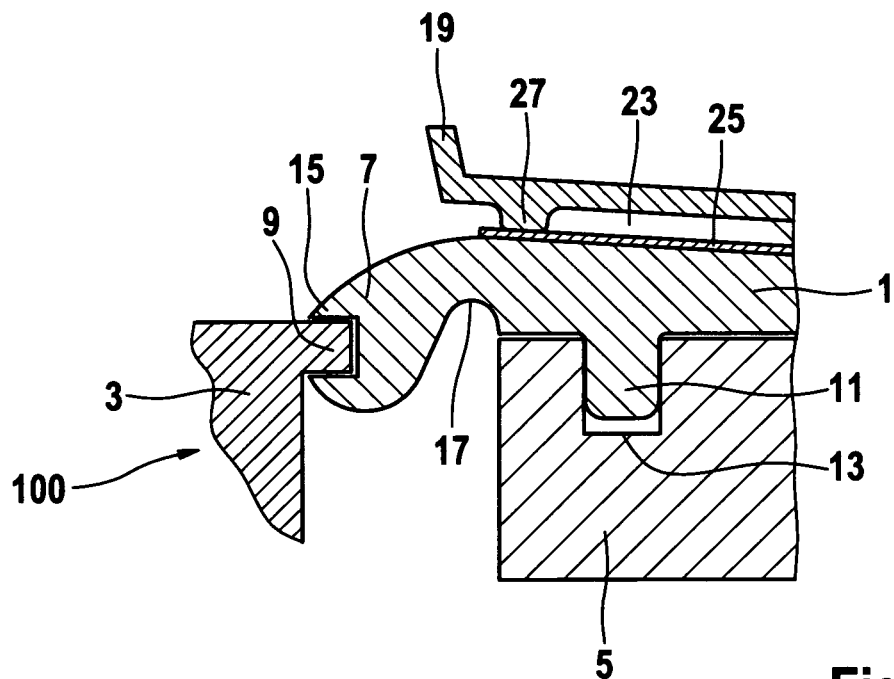
FIG. 4 shows a partial sectional view in a lateral area of a sealing device in accordance with a fourth embodiment of the present invention that is connected to the arrangement and to an external functional device.

FIG. 4 shows a sectional view of a detail of a sealing device 1 in accordance with a fourth embodiment of the present invention, that is connected to the arrangement 100 and to an external functional device 19.

The sealing device 1 in accordance with the fourth embodiment substantially corresponds to the one of the third embodiment. It is different from the third embodiment in that despite the vacuum seal 21 at the sealing device 1, a vacuum seal 27 is provided at the external functional device 19 for sealing the interstice 23. The vacuum seal 27 exemplarily is configured as a sealing bead.

Figure 5:
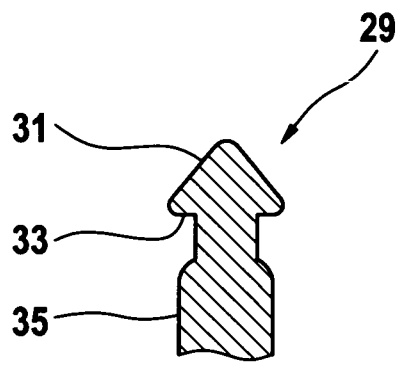
FIG. 5 shows a snap lock for use with the sealing device of the present invention.

FIG. 5 shows a snap-action device 29 or a part thereof having the form of a pin. The snap-action device 29 includes an insertion ramp 31, an undercut 33, as well as a portion 35 for orienting and/or positioning the external functional device (not shown). The insertion ramp 31 enables a simple introduction of the pin into an opening, and with the aid of the undercut 33 the pin may be snapped into the opening and retained therein. The portion 35 may ensure an orientation or positioning of the external functional device while it is being snapped on.

A snap-action device 29 such as, e.g., the pin shown in FIG. 5, may also be part of the sealing device 1 and effect its orientation and/or snap connection at the external functional device 19 or at a portion of the arrangement 100. A snap-action device 29 may form a tamper evidence closure in accordance with the above description or may be a part thereof.

Figure 6:
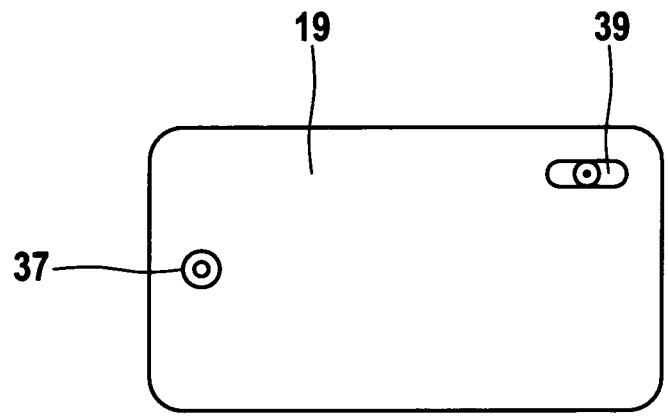
FIG. 6 schematically shows a device for positioning an external functional device in a top view of the sealing device of the present invention.

FIG. 6 shows a surface, e.g., a lower surface of a cassette as an example of an external functional device 19. On the surface a first positioning pin 37 is provided as a point of reference or origin of a coordinate system, and a second positioning pin 39 with an oblong hole for compensation of tolerances.

Figure 7:
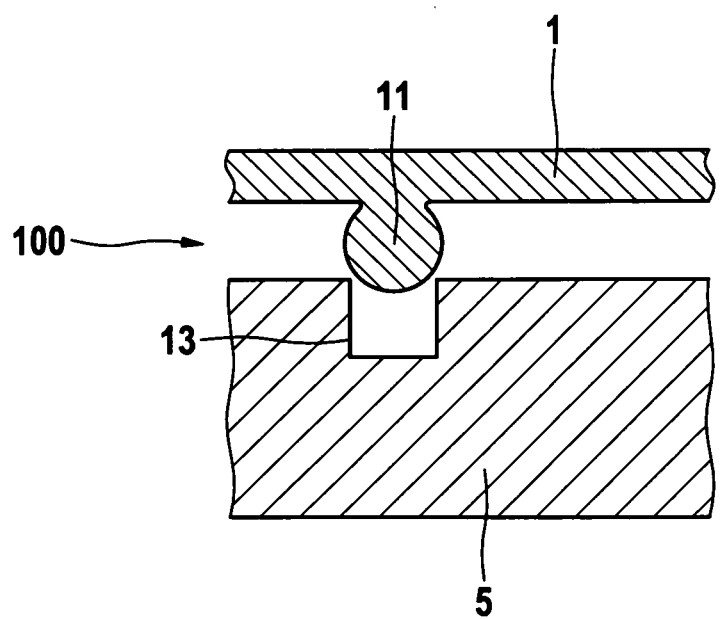

FIG. 7 shows a snap connection device of the sealing device 1 of the present invention including a third connection device 11, which has a reception portion 5 including a fourth connection device 13. In FIG. 7 the snap connection device is shown in a condition where it is not snapped on or connected, respectively.

Figure 8:
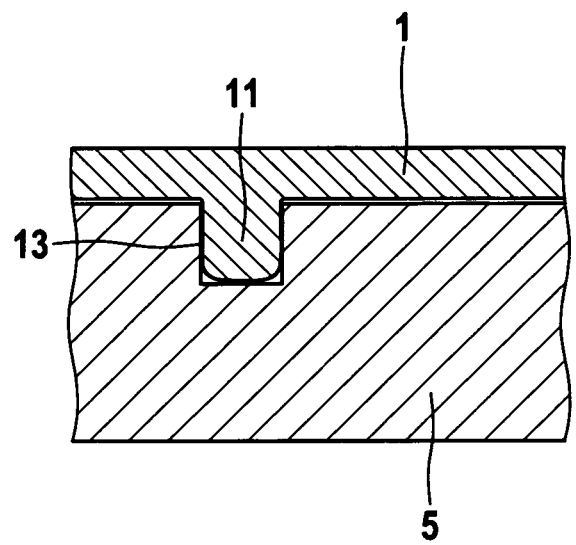

FIG. 8 shows the snap connection device of the sealing device 1 of the present invention of FIG. 7 in a condition where it is snapped on or connected, respectively. In a comparison of FIG. 7 with FIG. 8 it is clearly obvious that the third connection device 11 initially having the form of a partial circle in cross-section (see FIG. 7) has a different cross-sectional shape following snap connection (see FIG. 8). The change of shape contributes to the seal. It may preferably also contribute to fastening of the sealing device 1 to the reception portion 5.

Figure 9:
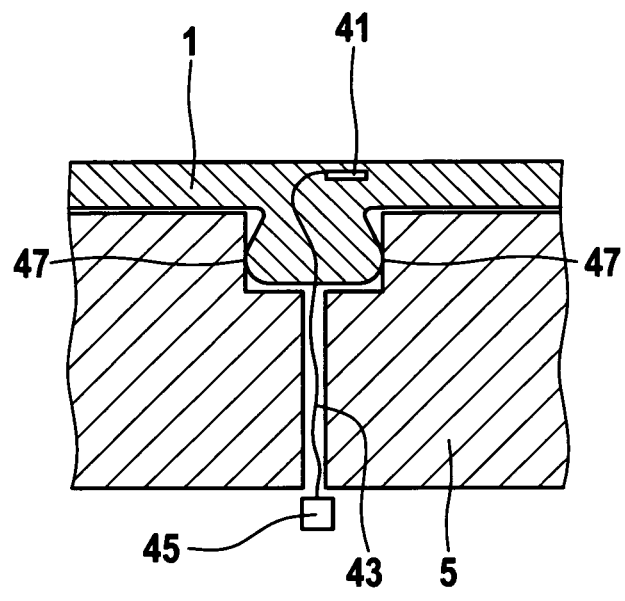
FIG. 9 shows a sealing device of the present invention with a sensor in cross-sectional view.

FIG. 9 shows a cross-sectional view of a sealing device 1 of the present invention including a sensor 41. As shown in FIG. 9, the sensor 41 is embedded in the interior of the sealing device 1. It may be configured as a temperature sensor. The sensor 41 is connected to an outside of the sealing device 1 by means of a feed line 43. In FIG. 9 it includes a plug connector 45 for establishing a signal communication.

In the locations designated by reference numeral 47, a vacuum seal is established by means of the snap connection shown in FIGS. 7 and 8.

Figure 10:
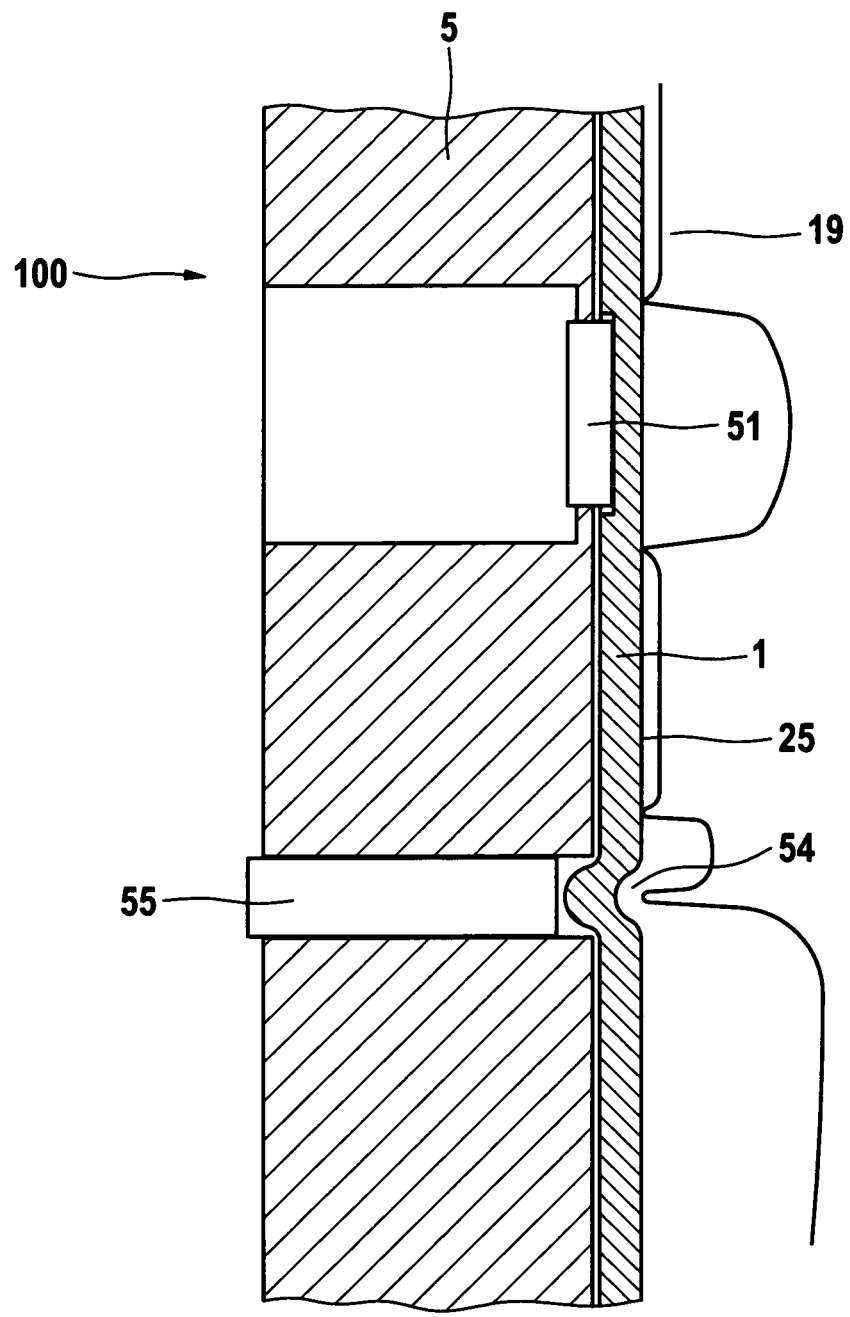
FIG. 10 schematically shows the connection between a reception portion between the sealing device and the external functional device in a horizontal section.

FIG. 10 schematically shows the structure of a reception portion 5, of the sealing device 1, and of the external functional device 19 in a horizontal sectional view.

The reception portion 5 includes a sensor 51 (here: a pressure sensor) and a tappet 55. The tappet 55 may be a valve tappet.

By movements of the tappet 55 with the aid of a phantom valve 54 in the sealing device 1 it is possible to generate a negative pressure for retaining the sealing device 1.

Examples of sensors 51 of the reception portion 5 include, irrespective of further features of the respective embodiment and without being limited hereto as sensors provided on the machine which measure through the sealing device, e.g., a capacitative level detector for the single-needle chamber of the external functional device, pressure sensors, ultrasound sensors, optical sensors and the like.

Figure 11:
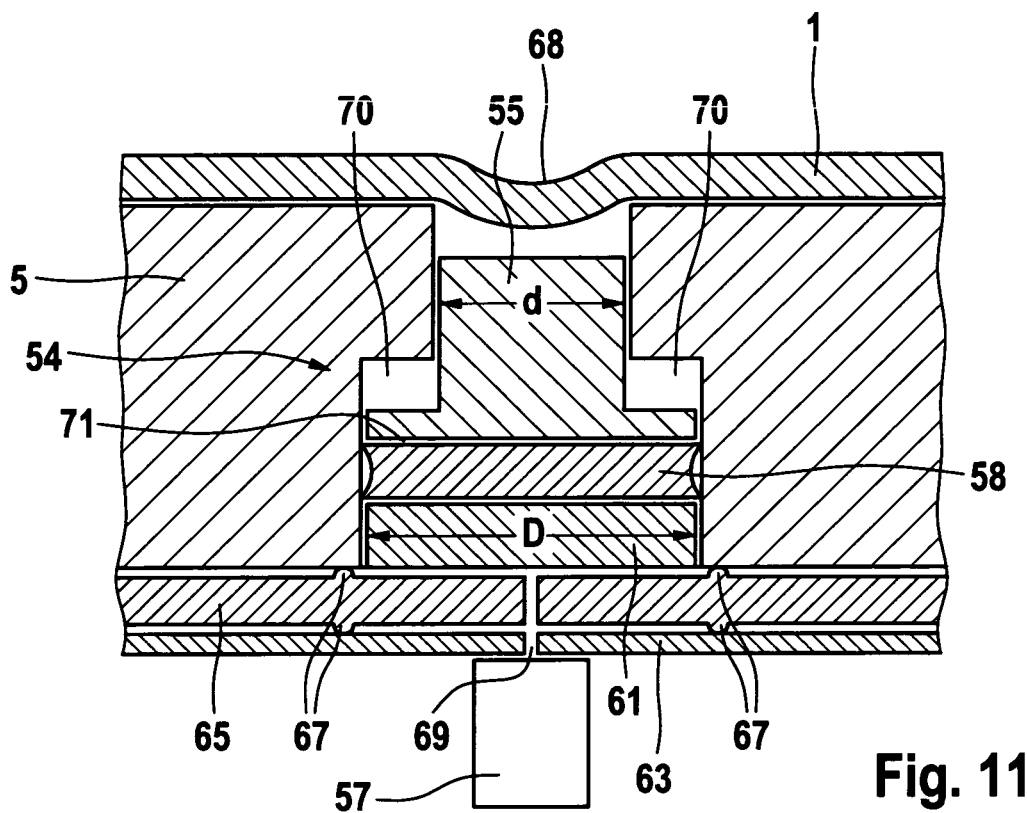
FIG. 11 shows a horizontal sectional view of a phantom valve actuator of a first embodiment.
Figure 12:
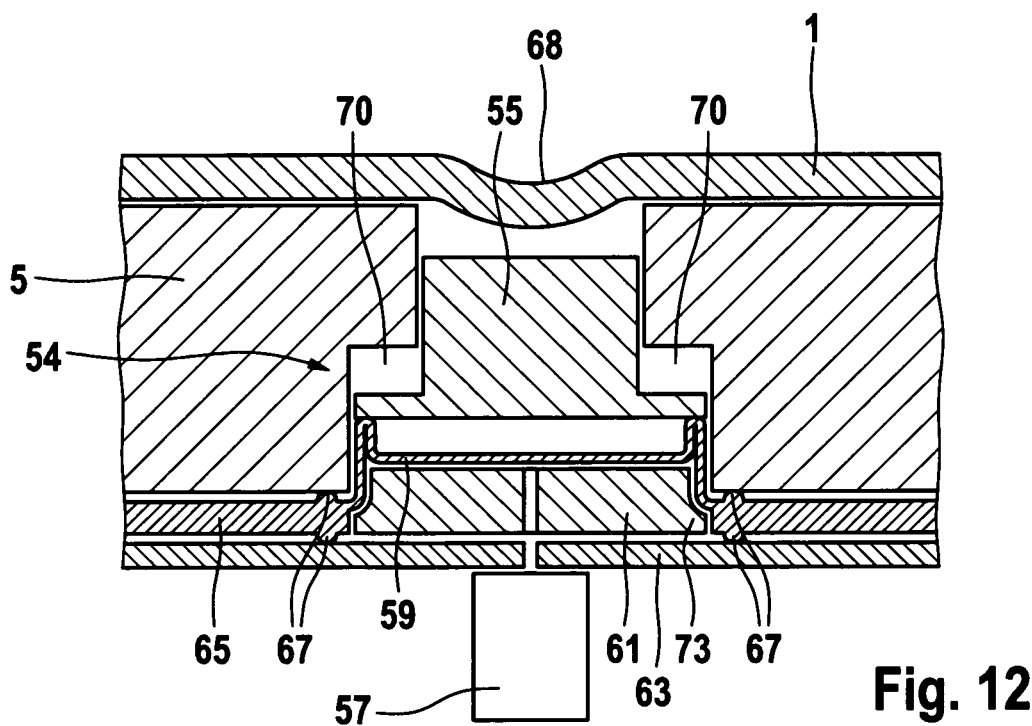
FIG. 12 shows a horizontal sectional view of a phantom valve actuator of a second embodiment.

FIGS. 11 and 12 show respective horizontal sectional views of a phantom valve actuator in a first and a second embodiment thereof.

The tappet 55 is movable by means of transmission of force by a valve 57. The valve 57 may be a pilot control valve. The tappet 55 is configured in a T shape. The diameter d of the tappet 55 in the longer portion of the T-shape may for example be 5 mm to 40 mm, preferably 18 mm (in the case of an SN valve) or 5 mm to 25 mm, preferably 9 mm (in the case of a substituate valve).

A disc-shaped element 58 is provided which has two annular peripheral projections. The two annularly peripheral projections act in a radial direction against the cylinder inner wall. In accordance with the present invention, a different number of annularly peripheral rings or annularly peripheral projections may be provided, e.g., one ring, three rings, or more.

Moreover a filler body 61 is provided. The filler body 61 may have a diameter D of, e.g., 10 mm to 60 mm, preferably 25 mm (SN valve), or for instance of 10 mm to 50 mm, preferably 16 mm (substituate valve). Between the valve 57 and the filler body 61 an air distribution plate 63 and a sealing mat 65 having sealing beads 67 are provided.

Actuation of the phantom valve actuator may effect a deformation 68 of the sealing device 1.

Via an opening 69, the valve 57 may suck in, or supply, air or gas. In its downward or upward movement in FIG. 11 the tappet 55 may pull the sealing device 1 downwards or push it upwards, or permit its movement in an upward direction.

As the disc-shaped element 58 acts against the cylindrical inner wall in the manner of, or as, radially acting seal rings, the tappet 55 is not free in its movement within the bore or blind hole 70.

Due to the disc-shaped element 58, a gas- or airtight space 71 may be created which allows the generation of a negative pressure.

With the aid of the air distribution plate 63, a negative pressure for exerting suction on the sealing device 1 or a pressure above atmospheric for raising the sealing device 1 is generated in predetermined locations only.

The bore or blind hole 70 is surface-treated in an appropriate manner at its cylindrical inner wall, e.g., preferably burnished or polished, in order to obtain a preferred surface quality for the disc-shaped element 58 sliding along, for an appropriate seal.

FIG. 12 shows a horizontal sectional view of a second embodiment of a phantom valve actuator.

An actuator diaphragm 59 is provided which may serve as a sealing device. Unlike the embodiment of FIG. 11, the sealing mat 65 in FIG. 12 is configured jointly with the integrated actuator diaphragm 59. The filler body 61 furthermore includes stops 73.

The actuator diaphragm 59 integrated into the sealing mat 65 is adapted to expand under pressure and push the tappet 55 upwards in the reference system of FIG. 12 or hold it up, respectively. Under negative pressure, the actuator diaphragm 59 may contract or collapse and pull the tappet 55 downward in the reference system of the figure, or admit its movement in this direction, respectively. In this way the sealing device 1 may be domed but at least sucked in.

In an arrangement according to FIG. 12, the tappet 55 may move freely inside the blind bore 70 in the axial direction of the latter.

In this embodiment, there are no particular requirements to the surface quality at the cylindrical inner wall of the bore or blind bore 70, which may advantageously simplify the process of manufacturing the blind hole 70.

The phantom valve actuators represented in FIGS. 11 and 12 operate with stops. I.e., the displacement path of the tappet 55 is limited by the stops 73 in the reception portion 5. Accordingly, a planar surface preferably results under the sealing device 1.

The displacement path of the tappet 55 may, however, also be unlimited. In an embodiment that is not represented here, the displacement path may only be limited against the external functional device 19 by pressing of the sealing device 1 in the valve area. In this way a secure pressing in the area of the valves may advantageously be ensured.

Figure 13:
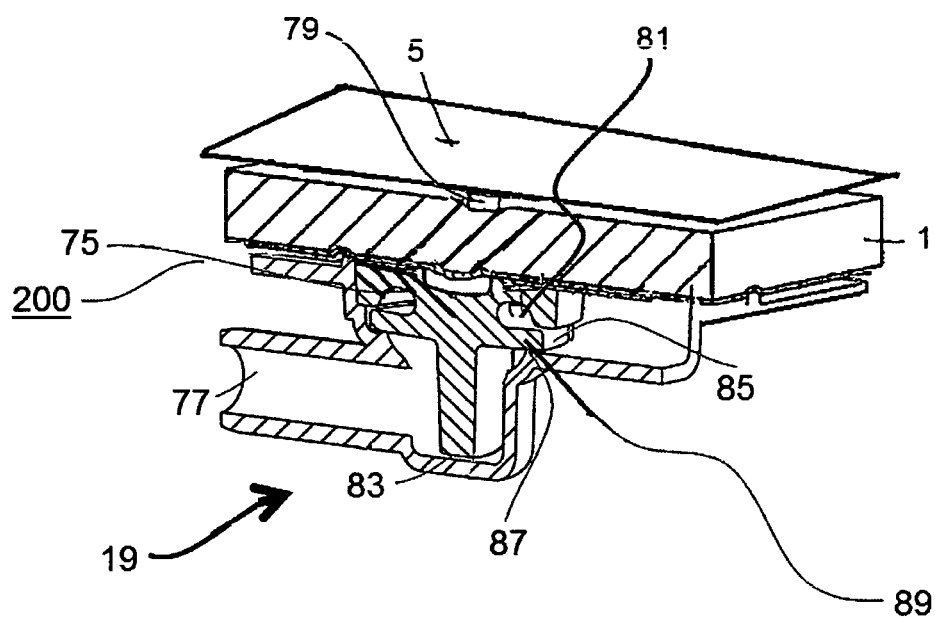
FIG. 13 shows schematically simplified a cut section of a valve device which is coupled to a sealing device according to the present invention.

FIG. 13 shows schematically simplified a cut section of a valve device 200 in a valve state of a closed check valve.

The valve device 200 is part of an external functional device 19 and comprises a valve core 75 which is arranged in a flow channel 77 of the external functional device 19.

As is shown in FIG. 13, the external functional device 19 is arranged in the arrangement (not shown here) for its use such that a bolt 79 of the reception portion 5 is arranged over or across a deformation space 81 of the valve device 200 or so as to have an effect on the deformation space 81.

Upon coupling the external functional device 19 to the sealing device 1, the bolt 79 of the reception portion 5, e.g., of an actuator-sensor plate, locally pushes against the sealing device 1 so that it is buckled in the direction towards the external functional device 19 and pushes the valve core 75 up to a stop 83 into the hard part of the external functional device 19.

In the illustrated check valve position, an elastic sealing ring 85 of the valve core 75 pushes against a rigid sealing ring 87 of the hard part of the external functional device 19 so that a gap 89 is closed. Thus, no fluid can flow through the flow channel 77 of the external functional device 19.

The present invention is not restricted to the embodiments described in the foregoing; the described embodiments only serve the purpose of illustration.

The invention claimed is:

1. A blood treatment apparatus, comprising:
    a sealing device comprising at least one first connection device and a third connection device; and
    an arrangement configured to treat at least one medical fluid, wherein the arrangement is configured as a hemodialysis apparatus, a hemofiltration apparatus, or a hemodiafiltration apparatus, the arrangement comprising:
        a supporting device including a second connection device; and
        a reception portion including a fourth connection device, wherein:
            the supporting device and the reception portion are mounted to the arrangement,
            the at least one first connection device of the sealing device is configured to be connected to the second connection device of the supporting device of the arrangement,
            the third connection device of the sealing device is configured to be connected to the fourth connection device of the reception portion of the arrangement,
            the reception portion is configured to receive at least one disposable cassette for conducting medical fluids,
            the sealing device is configured to seal a gap formed between the supporting device and the reception portion from an exterior of the treatment apparatus, the gap remaining after the gap is sealed by the sealing device, and
            wherein a fluid-tight seal is produced by at least one of: (i) the at least one first connection device together with the second connection device and (ii) by the third connection device together with the fourth connection device.

2. The blood treatment apparatus according to claim 1, wherein the first connection device is configured to be connected to the second connection device via a frictional connection, a form closure connection, or both.

3. The blood treatment apparatus according to claim 1, wherein the first connection device is insertable in the second connection device, wherein the second connection device is configured for receiving the first connection device.

4. The blood treatment apparatus according to claim 1, wherein the second connection device is insertable in the first connection device, wherein said first connection device is configured for receiving the second connection device.

5. The blood treatment apparatus according to claim 1, wherein at least one of the first connection device, the second connection device, the third connection device, and the fourth connection device has a peripheral configuration.

6. The blood treatment apparatus according to claim 1, wherein at least one of the first connection device, the second connection device, the third connection device, and the fourth connection device is configured as a sealing lip.

7. The blood treatment apparatus according to claim 1, wherein the first connection device in at least one portion of the sealing device has a lower thickness than in another portion of the sealing device.

8. The blood treatment apparatus according to claim 1, wherein the sealing device covers at least one portion of a surface of the reception portion.

9. The blood treatment apparatus according to claim 8, wherein the sealing device is configured to cover the entire surface of the reception portion during use.

10. The blood treatment apparatus according to claim 1, wherein the third connection device is configured to be connected to the fourth connection device via a frictional connection, a form closure connection, or both.

11. The blood treatment apparatus according to claim 1, wherein the third connection device or the fourth connection device includes at least one knob or is configured as a knob.

12. The blood treatment apparatus according to claim 1, wherein the sealing device is configured to be connected to a surface of the reception portion by the application of a negative pressure.

13. The blood treatment apparatus according to claim 1, wherein the sealing device is configured for a non-releasable connection to the arrangement.

14. The blood treatment apparatus according to claim 1, wherein the sealing device in at least one portion has predeformed areas which are configured by weakened sections or reinforcements of a thickness of areas surrounding the predeformed areas.

15. The blood treatment apparatus according to claim 14, wherein the predeformed areas are configured to perform a valve function.

16. The blood treatment apparatus according to claim 1, wherein the sealing device is configured for functional coupling to the at least one disposable cassette for conducting medical fluids.

17. The blood treatment apparatus according to claim 1, wherein the sealing device further comprises at least one of a sensor or portion thereof, an actuator or portion thereof, or a conduit or portion thereof.

18. The blood treatment apparatus according to claim 17, wherein the at least one of a sensor or portion thereof, an actuator or portion thereof, or a conduit or portion thereof is connected to the sealing device in at least one of a frictional connection, a form closure connection or an integral manner.

19. The blood treatment apparatus according to claim 1, wherein the sealing device further comprises at least one receptor for receiving a fastening device of the disposable cassette for conducting medical fluids, of the reception portion, or of both.

20. The blood treatment apparatus according to claim 1, wherein the sealing device is configured as a multi-component sealing device.

21. The blood treatment apparatus according to claim 1, wherein the sealing device includes at least one elastomer material or is comprised thereof.

22. The blood treatment apparatus according to claim 1, further comprising:
the at least one disposable cassette.

23. The blood treatment apparatus according to claim 22, wherein the sealing device is configured to be connected to the at least one disposable cassette.

* * * * *

UNITED STATES PATENT AND TRADEMARK OFFICE
CERTIFICATE OF CORRECTION

PATENT NO. : 9,827,358 B2
APPLICATION NO. : 13/255658
DATED : November 28, 2017
INVENTOR(S) : Goetz Günther et al.

Page 1 of 1

It is certified that error appears in the above-identified patent and that said Letters Patent is hereby corrected as shown below:

On the Title Page

Column 1, Line 1 (PCT Filed), delete "Mar. 10, 2010" and insert --Mar. 09, 2010--.

Signed and Sealed this
Tenth Day of April, 2018

Andrei Iancu
*Director of the United States Patent and Trademark Office*